United States Patent
Parab

[11] Patent Number: 5,326,566
[45] Date of Patent: Jul. 5, 1994

[54] USE OF DIBUTYL ADIPATE AND ISOPROPYL MYRISTATE IN TOPICAL AND TRANSDERMAL PRODUCTS

[75] Inventor: Prakash V. Parab, Williamsville, N.Y.

[73] Assignee: Bristol-Myers Squibb Company, New York, N.Y.

[21] Appl. No.: 108,279

[22] Filed: Aug. 19, 1993

Related U.S. Application Data

[63] Continuation-in-part of Ser. No. 89,069, Jul. 7, 1993, abandoned, which is a continuation-in-part of Ser. No. 790,939, Nov. 12, 1991, abandoned, which is a continuation-in-part of Ser. No. 701,944, May 17, 1991, abandoned.

[51] Int. Cl.$^5$ ............................................. A61K 9/10
[52] U.S. Cl. ............................ 424/401; 424/78.02; 514/746; 514/947; 514/928; 514/969
[58] Field of Search ............... 424/401, 484, 78.02; 514/946, 947, 938, 969

[56] References Cited

U.S. PATENT DOCUMENTS

| | | | |
|---|---|---|---|
| 4,370,322 | 1/1983 | Busse et al. | 514/180 |
| 4,544,547 | 1/1985 | von Bittera et al. | 424/78.02 |
| 4,859,696 | 8/1989 | Kamiya et al. | 424/449 |
| 5,001,139 | 3/1991 | Lawtes et al. | 424/449 |

OTHER PUBLICATIONS

Chemical Abstracts 113(26):237556d.

*Primary Examiner*—Thurman K. Page
*Assistant Examiner*—Raj Bawa
*Attorney, Agent, or Firm*—Morton S. Simon

[57] ABSTRACT

The present invention relates to composition and methods for enhancing and/or controlling epidermal, dermal and transdermal penetration of topically applied pharmacologically active agents by use of dibutyl adipate, or a mixture of dibutyl adipate and isopropyl myristate.

17 Claims, 4 Drawing Sheets

USE OF DIBUTYL ADIPATE AND ISOPROPYL MYRISTATE IN TOPICAL AND TRANSDERMAL PRODUCTS

BACKGROUND OF THE INVENTION

1. Related Applications

This application is a continuation-in-part of copending application 08/089,069, filed Jul. 7, 1993, now abandoned, which in turn is a continuation-in-part of copending application Ser. No. 07/790,939, filed Nov. 12, 1991, now abandoned, which in turn is a continuation-in-part of copending application Ser. No. 07/701,944 filed May 17, 1991 and now abandoned.

2. Field of the Invention

The invention relates to the enhancement as well as the control of epidermal, dermal and transdermal penetration of various topically applied pharmacologically active agents utilizing dibutyl adipate or a mixture of dibutyl adipate ("DBA") and isopropyl myristate ("IPM").

3. Description of the Art

Intravenous infusion, intramuscular injection, buccal, oral, rectal routes, and so forth have been generally adopted as methods for administration of a wide variety of therapeutically active agents, such as antihypertensives, β-Blockers, antiarrhythmics, antianginal agents, vasodi lators, antiemetics, antibacterial, antifungals, corticosteroids, retinoids, progestins, estrogens, androgens, analgesics and anti-inflammatories. When these therapeutically active agents are administered to humans or warm blooded animals by such routes, they enter the circulatory system and produce the desired systemic therapeutic effect. However, it is well-known that the aforementioned methods of administration have certain disadvantages. For example, buccal and rectal administration often produce discomfort and aggravation to the patient. The intravenous and intramuscular routes are not only painful for the patient, but also must be performed by trained individuals. Oral administration, although generally acceptable by the patient, may have the disadvantages of poor absorption of the therapeutic agent from the gastrointestinal tract and/or degradation which may be caused by the acidic medium of the stomach, enzymes in the gastrointestinal tract, interaction with ingested food or by rapid metabolism by the liver through which the drug must pass before it enters the systemic circulation.

Recognizing these disadvantages, many investigators have used the transdermal route to deliver the therapeutically active agent into systemic circulation. Various therapeutic and cosmetic agents are used for the treatment of a number of skin conditions, for example, hydrocortisone for pruritus and erythema in atopic dermatitis, sulconazole nitrate for fungal infection of the skin, tretinoin for photoaging, and 5-fluorouracil for psoriasis and skin cancer. However, the skin of humans and other warm blooded animals provides an excellent barrier to the penetration of exogenous chemical substances. The outermost layer of the skin, the stratum corneum, offers maximum resistance to penetration, whereas the lower layers are relatively permeable. For the proper treatment of skin disorders or skin diseases, it is important that the pharmacologically active agent penetrate the stratum corneum and be made available at appropriate concentrations at the site of action which can be the stratum corneum, the viable epidermis, the epidermis-dermis junction, the dermis itself, or all the aforementioned layers of the skin, depending upon the type of disorder or disease condition.

In certain skin conditions such as ichthyosis, callus or plaque psoriasis, the stratum corneum is thicker and thus can provide a significantly greater barrier to penetration of the drug, thereby reducing its efficacy. Moreover, recent studies have shown that as people age their skin becomes more resistant to penetration by water soluble drugs. In a few disease conditions, such as psoriasis, the stratum corneum is not intact and hence is more permeable than normal skin. As the disease or condition improves, there will be restructuring of the barrier and therefore, the resistance to the permeation of the therapeutically active ingredient will increase.

To achieve a consistent supply of therapeutic active ingredient at the site of action during the treatment of skin diseases, it has been found that the use of penetration enhancer is essential. Investigators have turned to various enhancing agents, for example, dimethyl sulfoxide, dimethyl formamide, methyl decyl sulfoxide (U.S. Pat. No. 3,527,864), dimethylacetamide (U.S. Pat. No. 3,472,931), and N-alkyl-2 pyrrolidone (U.S. Pat. No. 3,696,516), for topical as well as systemic delivery of therapeutic active agents. However, the use of the aforementioned penetration enhancers is not without problems. For example, the use of dimethyl sulfoxide causes in animals a foul taste and body odor, burning and erythema on the skin, a reduction in the relucency of the lens cortex and tissue necrosis (Martindale, *The Extra Pharmacopoeia*, pages 1461-1463, Twenty-Seventh Edition, 1977). Dimethyl formamide and dimethylacetamide also cause a sensation of burning and erythema on the skin. As a result, there exists a need for a novel agent that enhances the absorption of therapeutic agents through the skin and is substantially devoid of the disadvantages and drawbacks that to date have characterized many prior art penetration enhancing agents.

The present invention discloses as such an agent, dibutyl adipate (DBA) and the combination of dibutyl adipate and isopropyl myristate (IPM).

Dibutyl adipate is marketed under the trade name CETIOL B ® (by Henkel Corporation) as a low fat emollient for cosmetic products. It is disclosed as being a solvent for lipid soluble substances and as possessing good spreading properties. It is also recommended for use in cosmetic products such as hair sprays, hair fixatives and hand and body day creams.

Harding, Sohail and Busse, *Clinical and Experimental Dermatology*, Vol. 10, page 13-21, 1985 (see also U.S. Pat. No. 4,370,322), have used dibutyl adipate in the cream and ointment formulation of clobetasol propionate. However, their aim was to reduce percutaneous absorption of clobetasol propionate by incorporating in the base an oil, such as dibutyl adipate, into which steroids would favorably partition and reduce percutaneous absorption. In essence, Harding et al teach use of dibutyl adipate to decrease skin penetration. This teaching would certainly lead one skilled in the art away from use of dibutyl adipate where enhancement of skin penetration is desired.

Busse et al, U.S. Pat. No. 4,370,322 teaches the use of DBA, or a mixture of DBA and IPM, to reduce skin permeation of oil-soluble steroidal anti-inflammatory agents. To accomplish such end, Busse et al teach that a degree of unsaturation of 3 to 5 is required. Busse et al do not teach the use of DBA, or a mixture of DBA and IPM, with a water-soluble therapeutic agent. Nor do Busse et al teach use of DBA, or a mixture of DBA and IPM, with a water-soluble therapeutic agent having minimal solubility in DBA or in a mixture of DBA and IPM. This is likewise true for the prior art in general.

Surprisingly, the present inventor found that DBA, or a mixture of DBA and IPM, enhances the skin permeation of both water-soluble and oil-soluble drugs. This is advantageous and surprising particularly since prior art skin permeation enhancers capable of increasing skin permeation of water-soluble drugs generally do not increase skin permeation of oil-soluble drugs. An example of this is decyl methyl sulfoxide.

Isopropyl myristate is known as a penetration enhancer for topical preparations. However, the present inventor is unaware of any prior art reference in which a synergistic effect was reported in skin penetration enhancement through use of a combination of DBA and IPM.

The present invention discloses that emollient solvents, such as dibutyl adipate, when used in an optimum amount, alone or in combination with isopropyl myristate, can surprisingly enhance as well as control, the epidermal, dermal and transdermal penetration of various topically applied pharmacological agents.

Various dermal effective pharmacological agents are known which can provide beneficial effects when applied topically to the skin to treat surface or subsurface diseases or for creating skin conditions which protect the skin from external factors. Other pharmacological agents are also known which can provide beneficial effects when absorbed into the systemic circulation. A composition of such systemically effective pharmacological agents in combination with dibutyl adipate, or a mixture of dibutyl adipate and isopropyl myristate, can greatly enhance the rate of penetration of agents through the skin and increase the amount absorbed into the systemic circulation. Thus, it is possible to have a systemic effect through topical application of said composition. The topical delivery of systemically effective pharmacological agents can be of significant advantage in cases where drugs produce gastric problems, are not well absorbed when given orally, or are rapidly metabolized in the liver, e.g. the "first pass" effect. In such cases, the use of topical delivery can give a systemic response at lower dosage than required orally. Topical delivery also avoids the disadvantages present in the intravenous route of administration, which might otherwise be required in order to achieve effective blood levels at reasonable dosage amounts. Such dermatological agents can be made more beneficial by enhancing their penetration through the protective layer of the skin in accord with the present invention.

SUMMARY OF THE INVENTION

The present invention relates to the enhancement as well as the control of epidermal, dermal and transdermal penetration of various topically applied preparations. More specifically, the invention relates to compositions and methods for enhancing and/or controlling epidermal, dermal and transdermal penetration of topically applied pharmacologically active agents by use of dibutyl adipate, or a combination of dibutyl adipate and isopropyl myristate.

An object of the present invention is to provide a novel agent for enhancing and/or controlling skin permeation of therapeutic agents.

It is also an object of the present invention to provide a novel agent which will enhance and/or control epidermal and dermal absorption of dermatological agents (that is, drugs affecting skin to give a cosmetic or therapeutic benefit) and enhance and/or control delivery of systemically active therapeutic agents through the skin and into the general circulation.

Another object of the invention is to provide an epidermal, dermal or transdermal penetration enhancing agent which is substantially devoid of side effects.

Yet another object of the invention is to provide a novel composition utilizing such novel enhancing agents, which formulations are useful for topical application.

Still another objective of the invention is to provide a method for enhancing the skin penetration of therapeutic agents.

Other objectives, features and advantages of the invention will be apparent to those skilled in the art upon a study of this disclosure and appended claims.

DETAILED DESCRIPTION OF THE INVENTION

It has been found that the dermal and transdermal penetration of a pharmacologically active compound can be substantially improved by incorporating the compound into a composition containing a dermal or transdermal penetration enhancing amount of dibutyl adipate or a mixture of dibutyl adipate and isopropyl myristate.

This unexpected effect is quite useful in that it allows one to improve the dermal and transdermal delivery of pharmacologically active compounds from the composition, thereby allowing one to achieve the same level of efficacy with a lower overall concentration of the pharmacologically active compound in the composition.

The objectives of the present invention can be achieved by employing an effective amount of dibutyl adipate or a mixture of dibutyl adipate and isopropyl myristate, as the penetration enhancing agent, in a composition of matter further comprising at least one therapeutic agent capable of having its penetration enhanced.

More specifically, the instant invention provides a single or multiple phase topical composition for enhancing skin penetration of a pharmacologically active agent, said composition comprising:

(a) a pharmacologically effective amount of a pharmacologically active agent capable of having its skin penetration enhanced, the active agent being primarily oil-soluble or primarily water-soluble, and (b) when the active agent is primarily oil-soluble, an oil phase containing a first solvent system comprising dibutyl adipate or a mixture of dibutyl adipate and isopropyl myristate, the solvent system being present from that amount required to solubilize the active agent in the oil phase and form a saturated solution of the active agent in the oil phase to that amount required to solubilize the active agent in the oil phase and form a saturated solution of the active agent in the oil phase plus at most an excess of an additional 50% of the solvent system, or (c) when the active agent is primarily water-soluble and minimally oil-soluble, a second oil phase containing a second solvent system comprising DBA, or a mixture of DBA and IPM, and a water phase, at least a portion of the active agent being soluble in the second oil phase, all or a portion of active agent not soluble in the oil phase being soluble in the water phase, any excess active agent, if present, being suspended in the composition.

It should be appreciated that a single phase composition is intended to encompass a solution or a semisolid ointment or gel while a two phase composition is intended to encompass an emulsion. The emulsion can be oil-in-water, water-in-oil, or a complex emulsion. Also intended to be encompassed as a two phase composition is a mixture of an oil phase and a water phase which on mixing, as for example by shaking, form an emulsion which is stable at least for a time sufficient to permit application to the skin.

The present invention also provides a method of obtaining, in a warm blooded mammal, a desired degree of skin penetration of a pharmacologically active agent capable of having its skin permeation enhanced, said method comprising contacting the skin of such mammal with a composition of the present invention and, prior to said contacting step, adjusting the amount of said solvent or said second solvent, or when a mixture of DBA and IPM is employed as either the solvent or the second solvent, adjusting the ratio of DBA:IPM present in the composition to that amount required to give a predetermined degree of skin penetration of the pharmacologically active agent during said contacting step.

The composition of the present invention may also contain other ingredients of the type commonly employed by those skilled in the art of formulating compositions for topical application. These may include, for example, carriers, emollients, surfactants, emulsifying agents, auxiliary emulsifiers, emulsion stabilizing agents, thickening agents, preservatives, chelating agents, fragrance(s), and/or other penetration enhancer(s).

A composition can be any suitable non-toxic or pharmaceutically acceptable topical carrier material or vehicle, such as a solution, suspension, emulsion, lotion, cream, gel, ointment, liposome, aerosol spray, polymeric gel, sol, cataplasm, plaster, patch, film, or tape preparation, all of which are well-known to those skilled in the art of topical pharmaceutical formulation.

The methods of this invention apply to topical compositions containing a wide variety of pharmacologically active agents including but not limited to:

antihypertensives, such as clonidine, α-methyldopa, captopril, spironolactone; antiangina drugs and vasodilators, such as nitroglycerin, isosorbide dinitrate and dipyridamole; β-Blockers, such as propranolol, bupranolol, timolol and nadoxolol; sex hormones, such as estrogens, androgens, estradiol, testosterone, and progesterone; antiasthma drugs, such as cromoglycic acid; antihistamines, such as tripelennamine, triprolidine, diphenhydramine and chlorpheniramine; antibiotics, such as penicillins, cephalosporins, tetracyclines, polymyxin B, bacitracin and novobiocin; antifungal agents, such as sulconazole, nystatin, amphotericin B and griseofulvin; deodorants, such as benzalkonium chloride and neomycin sulfate; antiulcer drugs, such as cimetidine and ranitidine; antispasmodics, such as dicyclomine hydrochloride; and other drugs effecting the gastrointestinal tract, such as atropine; NSAIDS (non-steroidal anti-inflammatory agents), such as aspirin, ibuprofen, phenylbutazone and indomethacin; analgesics, such as aspirin and ibuprofen; antipyretics, such as aspirin, ibuprofen, acetaminophen and phenacetin; steroids, such as hydrocortisone, prednisolone, betamethasone and triamcinolone; sympathomimetic amines, such as xylometazoline, phenylephrine and naphazoline; central nervous system active agents, such as amphetamine, phenylpropanolamine and butorphanol; diuretics, such chlorothiazide, hydrochlorothiazide and benzthiazide; antitussives, such as codeine, dextromethorphan and diphenhydramine; vasodilators, such as hydralazine, enalapril maleate and nitroglycerin; antiemetics, such as chlorpromazine and meclizine; compounds for treating motion sickness, such as promethazine, dimenhydrinate and meclizine; antipsoriasis compounds, such as anthralin, MC 903 and tretinoin; hair growth promoters, such as minoxidil; antiphoto-aging compounds, such as retinoids and arotinoids; protein and peptide drugs, such as insulin, TGFα and TGFβ; antiviral drugs, such as acyclovir; drugs to treat ichthyosis, such as ammonium lactate; drugs to treat disturbed keratinization of skin, such as α or β hydroxycarboxylic acid and related ketocarboxylic acid and ester, lactones or salt forms thereof; and drugs to treat hyperpigmentation of skin, such as hydroquinone and 4-hydroxyanisole.

Preferably the pharmacological agent is from about 0.001% to about 80%, by weight, based on the total weight of the composition. However, the effective amount of a specific pharmacological agent will vary in accordance with parameters well understood by the physician or veterinarian. These parameters include the condition being treated, the age, weight and physical condition of the subject, and of course, the specific agent selected.

The optimum level of DBA, or mixture of DBA and IPM, may be readily evaluated by a few simple tests, such as those described herein.

In general, for a given label strength of a pharmacologically active agent that is primarily oil-soluble, it is preferred to use a minimum amount of solvent (DBA or DBA and IPM) to dissolve the drug completely and yet maintain a favorable partition coefficient and diffusion through the stratum corneum of the skin.

The general rate of penetration is in the order of: optimal solubilized solution (in other words, a saturated solution) is greater than that of a dilute solution. It is also necessary to consider the contribution of other solvents in the formulation on the solubility of the given strength of the pharmacologically active agent in the composition.

Included within the ambit of the present invention are two component compositions, the pharmacologically active agent (or drug) and the solvent.

When the drug is primarily oil-soluble the solvent can be exclusively DBA, the amount of DBA employed being such as to form a final composition which is saturated with respect to the drug or which contains sufficient solvent to form such saturated solution plus, at most, a 50% excess of the solvent (in this example, DBA). A three component composition is also envisioned. For example, the composition can comprise the primarily oil-soluble drug and a solvent consisting of a mixture of DBA and IPM. In such mixture the concentration of DBA and IPM depends upon the solubility of the drug in such solvent mixture.

Generally, for both primarily oil-soluble and primarily water-soluble drugs, the concentration of DBA is about 0.1% to about 99% and the concentration of IPM is from 0% to about 99%. The more preferred concentration of DBA is from about 0.1% to about 50%. The more preferred concentration of IPM is from about 1% to about 30%.

It should be noted that unless indicated to the contrary, all percentages of composition components recited herein are weight percentage (wt %) based upon the total weight of the composition.

Multicomponent compositions are also included with the scope of the present invention. In each such case it is necessary to consider the effect of each component added to the oil phase on the solubility of the drug in the oil phase of the composition. It may well be that a particular component added to the oil phase may decrease (or increase) the solubility of the drug in the oil phase so that it no longer satisfies the requirements of the present invention calling for sufficient DBA or a mixture of DBA and IPM to cause in the case of a primarily oil-soluble drug, the final oil phase to be saturated with respect to the drug or contain such amount of DBA or DBA and IPM plus, at most, a 50% excess of DBA or DBA and IMP. In such case, the amount of DBA or mixture of DBA and IPM employed would have to be appropriately adjusted.

The present invention will now be described with reference to the examples which follow. It should be noted, however, that the present invention is not deemed to be limited only to these examples.

EXAMPLE 1

In Vitro Skin Penetration Study

The following test method may be employed with human skin to determine epidermal, or dermal, or transdermal, penetration of pharmacologically active compounds used in the practice of this invention. The procedure is also applicable to skin of other warm blooded animals.

Skin Preparation

Normal excised human skin obtained from breast reduction or abdominal skin samples obtained from the Firefighters Skin Bank were used. The skin samples were stored in a freezer at −30° C. until needed. Only skin that appeared normal was used. Historical evidence of chronic illness, skin disease or skin injury excluded use of skin samples in the study.

The skin obtained from the Firefighters Skin Bank was supplied as sterile, split-thickness skin with most of the underlying dermis already removed. The skin was thawed and rinsed in normal saline for about 30 minutes prior to use.

The skin obtained from breast reduction autopsy was full thickness skin. It was thawed at room temperature in normal saline followed by freezing on a microtome with carbon dioxide and sectioning to a layer around 200 micrometers thick. It was then stored in normal saline at 5° C. until about 8 hours before use.

Skin Penetration

The skin sections were mounted on flat-top Franz diffusion cells with a diffusional cross-section of 0.636 cm$^2$ or 1.8 cm$^2$. A 50 or 100 microliter sample of test formulation was placed on the stratum corneum surface of the skin in the donor compartment and the receptor compartment was filled with 4 to 8 ml of normal saline or 30% isopropanol in water. The selection of receptor fluid depended on the drug candidate whose penetration had to be evaluated. The main objective was to maintain sink conditions in the receptor compartment. The receptor fluid was well stirred throughout the experiment and the temperature was maintained by circulating water at 37° C. through the water jacket of the diffusion cell. A 150 to 500 microliter sample was withdrawn from the receptor compartment at appropriate intervals and analyzed for drug content by HPLC or by scintillation counter for radioactive drug. The receptor fluid was replenished with normal saline after each withdrawal. All the receptor fluid and replenished fluid was thoroughly degassed before use.

EXAMPLE 2

Halobetasol propionate (BMY 30056) is an ultra-potent primarily oil-soluble steroid used topically for the treatment of dermatological conditions such as eczema and psoriasis. Halobetasol propionate is commercially available by Bristol-Myers Squibb as ULTRAVATE® Cream and ULTRAVATE® Ointment. The composition of these commercial products and also several experimental formulations are given in Table 1 and Table 2. ULTRAVATE® Cream is an oil-in-water emulsion containing isopropyl palmitate and isopropyl isostearate as emollients. The ULTRAVATE® Ointment is a nonaqueous emulsion of propylene glycol in a petrolatum base. The in vitro human skin penetrations of these two compositions and experimental formulation FN8-1089-25 cream are given in Table 3, under Study I. It is observed that the ULTRAVATE® Cream has lower skin penetration than ULTRAVATE® Ointment. The presence of the emollients isopropyl palmitate and isopropyl isostearate, which are known to have a similar penetration enhancement affect as isopropyl myristate, did not enhance the penetration of halobetasol propionate from ULTRAVATE® Cream as compared to ULTRAVATE® Ointment. The increase in skin penetration of halobetasol propionate from ULTRAVATE® Ointment may be due to the presence of the penetration enhancer, propylene glycol, as well as occlusion provided by petrolatum. Experimental cream FN8-1089-25, having 15 wt % dibutyl adipate (DBA) and 7 wt % propylene glycol (PG), showed poor penetration compared to ULTRAVATE® Ointment and was not superior to ULTRAVATE® Cream. One possible explanation for the poor penetration of this experimental formulation is that due to the dibutyl adipate there may have been oversolubilization of halobetasol propionate in the oil phase of the cream vehicle and this may have caused reduction of partitioning of halobetasol into the skin. This may explain the results of Harding et al. (Clinical and Experimental Dermatology, Vol. 10, page 13-21, 1985) who, when using 18 wt % DBA and 10 wt % PG in a clobetasol propionate cream formulation, observed reduced penetration of clobetasol propionate.

The present invention is based on the finding that with primarily oil-soluble drugs, DBA and the mixtures of DBA and IPM reduce percutaneous absorption of a therapeutic agent only when such solvent system is used in a concentration which oversolubilizes the drug in the oil phase of the formulation. Surprisingly, when a concentration of DBA or a mixture of DBA and IPM is used, under circumstances defined by the present invention, the skin penetration of a primarily oil-soluble active is unexpectedly increased, not decreased as would be expected from the teaching of Harding et al. The operative determinant is the formation of a saturated solution to not more that a 50% excess there over, as will be explained in greater detail hereinafter.

In a different human skin study, the in vitro skin penetration of halobetasol propionate from ULTRAVATE® Ointment, FN8-1114-16 cream and FN8-1114-13 cream, was evaluated (see Table 3, Study II). ULTRAVATE® Ointment was used as a control in order to normalize the data, and to assist in the comparison of skin penetration of different formulations when evaluated for skin penetration in different human skin. The rank order of penetration at 72 hours is ULTRAVATE® ®Ointment>FN8-1114-16 cream>FN8-1114-13 cream.

ULTRAVATE® Cream contains isopropyl palmitate and isopropyl isostearate, which are reported to have skin penetration enhancement properties similar to isopropyl myristate (IPM). However, ULTRAVATE® Cream containing these fatty acid esters shows poor penetration in comparison to ULTRAVATE® Ointment (see Table 3, Study I). Cream formulation FNS-1114-16 (containing 6 wt % IPM and 2 wt % DBA) shows about a five-fold increase in skin penetration as compared to ULTRAVATE® Cream (compare results from Study I and Study II, Table 3) and has about four-fifths of the penetration of ULTRAVATE® Ointment.

Cream formulation FN8-1114-13 (containing 6 wt % IPM+2 wt % DBA+23 wt % PG) showed about 3 times more penetration than ULTRAVATE® Cream but was not superior to ULTRAVATE® Ointment or to cream FN8-114-16.

It can be concluded from Study I and Study II that: (a) by sing optimum amounts of DBA and IPM, which are just sufficient to dissolve halobetasol propionate in the oil phase of the cream, one can enhance the skin penetration of halobetasol propionate, (b) inclusion of PG, a known penetration enhancer, in the formulation containing optimum amounts of DBA and IPM does not improve the skin penetration of halobetasol propionate any further, and (c) a mixture of DBA and IPM in the new cream formulation showed better skin penetration of halobetasol propionate than ULTRAVATE® Cream having a mixture of isopropyl isostearate and isopropyl palmitate. Hence, the combination of DBA and IPM affords a superior skin penetration enhancement than isopropyl isostearate, isopropyl palmitate or IPM.

Figure 1:
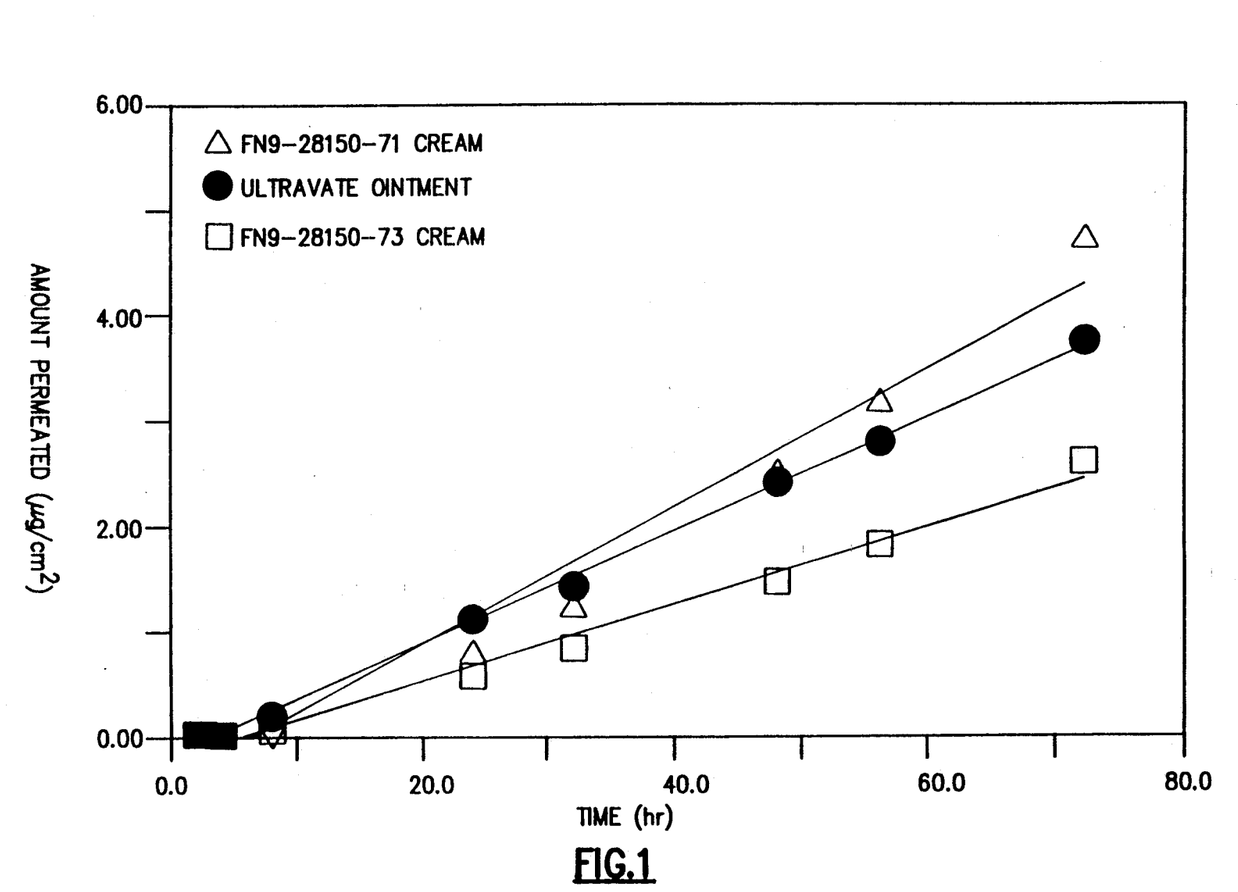
FIG. 1 shows the skin penetration of halobetasol propionate from FN9-28150-73 cream, FN9-28150-71 cream and Ultrarate ® Ointment.

The in vitro skin penetration of ULTRAVATE® Ointment (control) and experimental creams FN9-28150-71 and FN9-28150-73 was evaluated in another experiment (see Study III, Table 3, FIG. 1). The rank order of penetration at 72 hours is FN9-28150-71 cream->ULTRAVATE® Ointment>FN9-28150-73 cream FN9-28150-71 cream contains 0.5 wt % DBA and 10wt % IPM as solvents in the oil phase. This solvent mixture results in a saturated solution of 0.05 wt % of halobetasol propionate in the oil phase of the cream formulation. This cream showed about 7.5 times more enhanced skin penetration than ULTRAVATE® Cream and was slightly better than ULTRAVATE® Ointment (Compare Study III with Study I, in Table 3).

FN9-28150-73 cream contains 4 wt % DBA and 10 wt % IPM as solvents in the oil phase. The solvent concentration in this formulation is slightly in excess of what is necessary to dissolve the given strength of halobetasol propionate in the oil phase. The oil phase of the formulation had a degree of unsaturation of 1.5%. It gave comparatively less skin penetration than the cream having its oil phase saturated with respect to the active (FN9-28150-71 cream).

A degree of unsaturation of 1.5 means that the amount of DBA, or DBA and IPM, present in the oil phase is one and a half times the amount required to dissolve the halobetasol propionate in the oil phase of the composition so that the final oil phase of the composition is saturated with respect to the halobetasol propionate, plus contains a 50% excess of such solvent(s). To be more specific, when unsaturation is referred to herein relative to a particular pharmacological active, it means that the oil phase of the composition contains the solvent system of the present invention in an amount from about that which is sufficient to produce a saturated solution of such pharmacological active relative to the total oil phase of the composition (this represents a degree of unsaturation of 1) to a like amount plus at most a 50% surplus of such solvent(s) (this represents a degree of unsaturation of 1.5).

Thus, a degree of unsaturation of 1.5 means that the oil phase of the final formulation contains 1½ times the amount of solvent system of the instant invention needed to saturate the oil phase of the final formulation with respect to a particular pharmacological active dissolved in the oil phase therein.

Naturally, the amount of solvent system needed will depend on the particular pharmacological active employed. As will be seen from the Examples of the present application, in order to produce a final composition containing 0.05% halobetasol propionate, with the oil phase of such final composition being saturated relative to the halobetasol propionate, it is required that the oil phase contain 0.5 wt % DBA and 10 wt% IPM. Since the oil phase of the final formulation contains just that amount of the solvent system of the instant invention required to render the oil phase of the final formulation saturated relative to halobetasol propionate and no excess of such solvent, the oil phase of the final formulation is said to have a degree of unsaturation of 1.

An unsaturation value of 1.5 means the oil phase of the final composition contains more of the solvent system of the present invention than the minimum required to make such oil phase saturated, saturation of course being relative to the halobetasol propionate. The 1.5 unsaturation value indicates the oil phase of the final composition contains 1½ times the amount of solvent system required to produce a final composition the oil phase of which is saturated with respect to halobetasol propionate (in other words, the oil phase of the final composition contains a 50% surplus of the solvent system of the invention).

The present inventor surprisingly discovered that, for primarily oil-soluble drugs, optimum penetration occurs at an unsaturation value of 1 and falls as one approaches an unsaturation value of 1.5. Unsaturation values over 1.5 are impractical for primarily oil-soluble drugs, for skin penetration enhancement purposes.

These findings are surprising and not predictable from Harding et al. who teach only that an unsaturation value of over 3 decreases penetration enhancement of the primarily oil-soluble active substance.

One skilled in the art would learn nothing from Harding et al that would lead one to believe that DBA or a mixture of DBA and IPM would have an opposite affect at low unsaturation values and would be optimized from an unsaturation value of 1 to an unsaturation value of 1.5. One skilled in the art would in no way learn that the operative range of unsaturation is 1 to 1.5, as discovered by the present inventor. Still further, one would not learn that DBA synergizes the skin penetration enhancing effect of IPM. This finding was also entirely unexpected.

In general, as compared to cream formulations, petrolatum-based ointments afford superior skin penetration of pharmacological active agents contained therein. This is due to the occlusive nature of such ointments. The present invention enables one skilled in the art to formulate cream formulations containing pharmacological active(s) and having appropriate proportions of DBA or IPM and DBA in the oil phase, which afford skin penetration of the active(s) similar to, or better than that of, ointments containing such active(s).

Petrolatum-based ointments are greasy. In certain instances it may be desired to have cosmetically elegant (less greasy) topical products (such as creams, lotions, gels and solutions) having skin penetrations of the pharmacological active similar to that of an ointment. The present invention enables the formulator to attain this goal.

It is clear from the Examples (see FIG. 1) that it is possible to control the rate of skin penetration of a primarily oil-soluble pharmacological active by adjusting the degree of unsaturation by increasing or decreasing the amount of the solvent system in the oil phase or, when DBA and IPM are employed as the solvent system, adjusting the relative amounts of each in the oil phase (compare example FN9-28150-71 with FN9-28150-73). This is very useful in dermal and transdermal products as it enables one to control the rate of delivery of the drug to the site of action.

Figure 2:
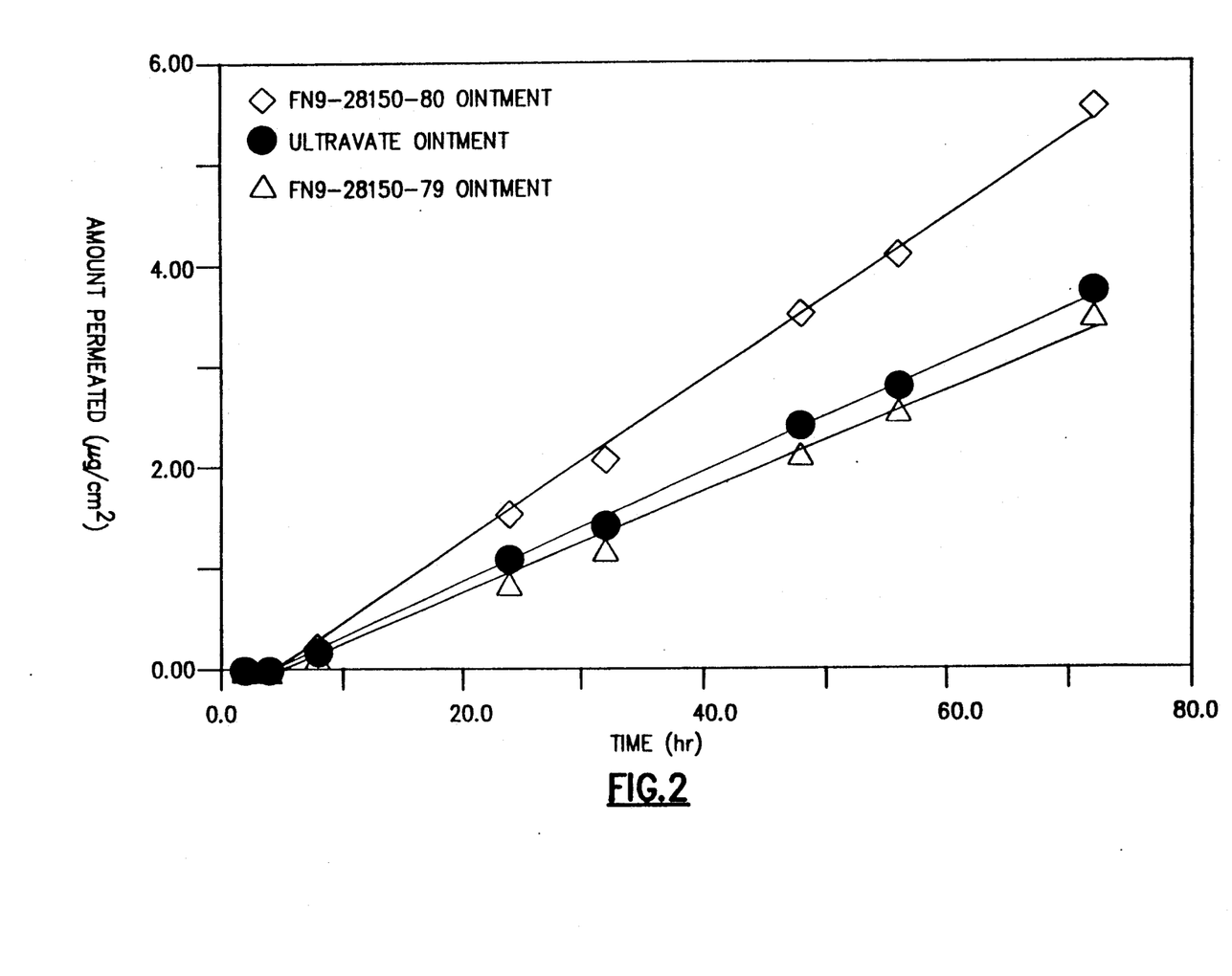
FIG. 2 shows the skin penetration of halobetasol propionate from FN9-28150-79 ointment, FN9-28150-80 ointment and Ultravate ® Ointment.

The in vitro skin penetration data of halobetasol propionate ointments FN9-28150-79 and FN9-28150-80, and commercial ULTRAVATE ® Ointment as a control are shown in FIG. 2, and Study IV of Table 3. The rank order of penetration is FN9-28150-80 ointment->ULTRAVATE ® Ointment≧FN9-28150-79 ointment.

FN9-28150-79 ointment contains 2 wt % DBA and 6 wt % IPM in an optimum amount, just enough to dissolve halobetasol propionate in the ointment formulation. This new ointment gave penetration similar to that of the ULTRAVATE ® Ointment containing PG as an enhancer.

FN9-28150-80 ointment is similar to FN9-28150-79 ointment but it contains ozokerite. This new cintment showed 1.5 times more penetration than ULTRAVATE ® Ointment or FN9-28150-79 ointment. This improved penetration is due to the use of an optimum mixture of IPM and DBA and may be due to the enhanced occlusion obtained by incorporating ozkerite in the ointment base.

It is a common practice to use PG as a penetration enhancer in dermal and transdermal preparations. PG, as discussed earlier, can be a sensitizer and irritant when applied topically. The side effects of PG are more pronounced in an occluded condition such as occurs in the application of an ointment or a transdermal patch (C. Huriez, P. Martin and M. Mennecier, L'allergie au propylene glycol, Rev. Franc. Allerg., Vol. 6: pages 200–205, 1966; M. Hannuksela, V. Pirila and O. P. Salo, Skin reactions to propylene glycol, Contact Dermatitis, Vol. 1: pages 112–116, 1975; S. Agren-Jonsson and B. Magnusson, Sensitization to propantheline bromide, trichlorocarbanilide and propylene glycol in an antiperspirant, Contact Dermatitis, Vol. 2: pages 79–80, 1976; and K. Motoyoshi, S. Nozawa, M. Yosimura and K. Matsada, The safety of propylene glycol and other humectants, Cosmet. Toilet., Vol. 99: pages 83–91, October 1984.)

The present invention demonstrates that by incorporating optimal amounts of dibutyl adipate or dibutyl adipate and isopropyl myristate into the oil phase of a topical formulation, the formulation can have the benefits of enhanced skin penetration of pharmacologically active compounds without the use of propylene glycol or the possible associated irritation or sensitization.

TABLE 1

Composition of 0.05 wt % halobetasol propionate commercial cream (ULTRAVATE ®) and experimental cream formulations.

| Ingredient | ULTRAVATE ® Cream* % w/w | FN8-1089-25 % w/w | FN8-1114-16 % w/w | FN8-1114-13 % w/w | FN9-28150-71 % w/w | FN9-28150-73 % w/w | Rationale |
|---|---|---|---|---|---|---|---|
| Halobetasol Propionate | 0.05 | 0.05 | 0.05 | 0.05 | 0.05 | 0.05 | Active ingredient |
| Dibutyl Adipate | — | 15.00 | 2.00 | 2.00 | 0.50 | 4.00 | Solvent/emollient |
| Isopropyl Myristate | — | — | 6.00 | 6.00 | 10.00 | 10.00 | Solvent/emollient |
| Isopropyl Isostearate | 3.00 | — | — | — | — | — | Solvent/emollient |
| Isopropyl Palmitate | 2.00 | — | — | — | — | — | Solvent/emollient |
| Propylene Glycol | — | 7.00 | — | 23.00 | — | — | Solvent |
| Steareth-213 | 3.00 | 2.50 | — | 2.50 | — | — | Emulsifying agent |
| Laureth-23 | — | — | 0.50 | — | 0.50 | 0.50 | Emulsifying agent |
| Steareth-2 | — | 2.50 | 2.50 | 2.50 | 2.50 | 2.50 | Emulsifying agent |
| Stearyl Alcohol | — | 3.00 | — | 3.00 | — | — | Thickening agent |
| Cetyl Alcohol | 6.00 | 4.00 | 1.60 | 4.00 | 1.60 | 1.60 | Thickening agent |
| Dimethicone 200 | — | 1.00 | 1.00 | — | 1.00 | 1.00 | Emollient |
| Petrolatum | — | — | 10.00 | 6.00 | 15.00 | 15.00 | Occlusive vehicle |
| Glycerin | 2.0 | — | 4.00 | — | 4.00 | 4.00 | Humectant |
| Trisodium Citrate | — | 0.14 | — | 0.14 | — | — | Buffering agent |
| Citric Acid | — | 0.07 | — | 0.07 | — | — | Buffering agent |
| Carbomer 934* | — | — | 0.25 | — | 0.25 | 0.25 | Thickening agent |
| Veegum K* | — | — | 0.30 | — | 0.30 | 0.30 | Thickening agent |
| Kathon CG* | 0.05 | 0.05 | 0.05 | 0.05 | 0.05 | 0.05 | Micropreservative |
| Germall II | 0.2 | 0.2 | 0.10 | 0.10 | 0.10 | 0.10 | Micropreservative |
| Na$_2$EDTA | — | — | 0.05 | — | 0.05 | 0.05 | Chelating agent |
| Sodium Hydroxide | — | — | 0.07 | — | 0.07 | 0.07 | pH adjustment |

TABLE 1-continued

Composition of 0.05 wt % halobetasol propionate commercial cream (ULTRAVATE ®) and experimental cream formulations.

| Ingredient | ULTRAVATE ® Cream* % w/w | FN8-1089-25 % w/w | FN8-1114-16 % w/w | FN8-1114-13 % w/w | FN9-28150-71 % w/w | FN9-28150-73 % w/w | Rationale |
|---|---|---|---|---|---|---|---|
| Water for production | 83.75 | 64.49 | 71.60 | 50.54 | 64.03 | 60.53 | Vehicle |

TABLE 2

Composition of 0.05 wt % halobetasol propionate commercial cream (ULTRAVATE ®) and experimental ointment.

| Ingredients | ULTRAVATE ® Ointment % w/w | FN9-28150-79 % w/w | FN9-28150-80 % w/w | Rationale |
|---|---|---|---|---|
| Halobetasol Propionate | 0.05 | 0.05 | 0.05 | Active Ingredient |
| Dibutyl Adipate | — | 2.00 | 2.00 | Solvent/emollient |
| Isopropyl Myristate | — | 6.00 | 6.00 | Solvent/emollient |
| Propylene Glycol | 7.50 | — | — | Solvent |
| Dehymuls E* | 7.50 | 7.50 | 7.50 | Emulsifying agent |
| Bees Wax | 5.00 | 7.50 | 2.50 | Thickening agent |
| Ozokerite | — | — | 5.00 | Occlusive vehicle |
| Petrolatum | 79.95 | 76.95 | 76.95 | Occlusive vehicle |

TABLE 3

In-vitro skin penetration of 0.05 wt % halobetasol propionate from different formulations.

| Formulation | Amount penetrated in 72 hours (micrograms)* | Amount penetrated in percentage relative to ULTRAVATE ® Ointment as Control |
|---|---|---|
| Study I | | |
| ULTRAVATE ® Ointment (PG 7 wt %) | 2.29 | 100.00 |
| ULTRAVATE ® Cream (Isopropyl isostearate 3 wt % + Isopropyl palmitate 2 wt %) | 0.38 | 16.59 |
| FN8-1089-25 cream (DBA 15 wt % + PG 7 wt %) | 0.35 | 15.28 |
| Study II | | |
| ULTRAVATE ® Ointment (PG 7 wt %) | 4.76 | 100.00 |
| FN8-1114-16 cream (DBA 2 wt % + IPM 6 wt %) | 3.9 | 81.90 |
| FN8-1114-13 cream (DBA 2 wt % + IPM 6 wt % + PG 23 wt %) | 2.15 | 45.16 |
| Study III | | |
| ULTRAVATE ® Ointment (PG 7 wt %) | 3.75 | 100.00 |
| FN9-28150-71 cream (DBA 0.5 wt % + IPM 10 wt %) | 4.75 | 126.00 |
| FN9-28150-73 cream (DBA 4 wt % + IPM 10 wt %) | 2.61 | 69.6 |
| Study IV | | |
| ULTRAVATE ® Ointment (PG 7 wt %) | 3.75 | 100.00 |
| FN9-28150-79 cream (DBA 2 wt % + IPM 6 wt %) | 3.48 | 92.80 |
| FN9-28150-80 cream (DBA 2 wt % + IPM 6 wt % + Ozokerite 5 wt %) | 5.57 | 148.50 |

*Amount in micrograms penetrated per cm² area of the skin. The results are average of multiple determinations.

EXAMPLE 3

Rhino Mouse Uterine Model To Evaluate Efficacy Of Retinoid Formulations

The skin of rhino mouse is characterized by the presence of numerous large cysts resembling comedones (S. J. Mann, Hairloss and cyst formation in hairless and rhino mutant mice, Anat. Rec., Vol. 170, pages 485-500, 1971) and is useful as a model system for the pharmacologic testing of agents, such as retinoids, for the treatment of acne (R. E. Ashton, M. J. Connor and N. J. Lowe, Histological changes in the skin of the rhino mouse induced by retinoids, J. Invest. Derm., Vol. 82: pages 632-635, 1984; E. J. Van Scott, Experimental animal integumental models for screening potential dermatologic drugs, in: Advances in Biology of the Skin, Vol. XII, *Pharmacology and the Skin*, W. Motagna, E. J. Van Scott and R. B. Stoughton, Editors, Meredith Corporation, N.Y., pages 523-531, 1972.) The experimental details of the model used to evaluate the efficacy of tretinoin formulations are given below.

Female rhino mice were obtained from the Skin and Cancer Hospital, Temple University, Philadelphia, Pennsylvania. Upon receipt, the rhino mice were treated with an anti-parasitic agent, trichlorfon (COMBOT ®), to rid them of pinworms. It was administered in their drinking water for two weeks. An additional two weeks was allowed to pass without COMBOT ® treatment before mice were placed on study. Animals were housed in accordance with the National Institute of Health guidelines and had free access to food and water. At the time of the study initiation, the mice were 9-14 weeks old.

The mice were individually housed in a plastic shoe box cage with corn cob bedding and placed in rooms illuminated with yellow lights, cycled for 12 hours on and 12 hours off during the study.

The mice were divided into groups of five and their contralateral flank sites were treated with 50 microliters of test formulation and vehicle or ethanol. One group of mice was run as a control with treatment of vehicle or ethanol. Animals were treated once a day for five days.

Two days after the last treatment, the animals were sacrificed by $CO_2$ inhalation and skin sections from the test and control sites were taken. Excessive fat and connective tissue from the subcutaneous region of the skin were removed using a scalpel. The skin was then placed on filter paper and a biopsy of ⅝" of the circular area of skin was removed by arch punch. The epidermal sheet from the biopsy was separated from the dermis after incubation in 0.5% acetic acid solution for 10-20 hours at 4° C. These sheets were then fixed in formalin, dehydrated with ethanol and cleared in xylene.

The sheets were then evaluated for changes in the sizes of the utriculi as follows: The maximum diameter of 20 representative utriculi per tissue sample were measured, using an IBM PC computer image measurement program (Microscience, Inc., Federal Way, Washington D.C.) and an Olympus microscope (200×magnification). Retinoid effects were evaluated as a percent reduction in uterine diameter by comparing mean diameter of the vehicle treated groups to that of formulation treated groups.

EXAMPLE 4

It should be noted that in this Example there is insufficient solvent to dissolve the primarily oil-soluble pharmacological active BMY 30047 in the oil phase of the cream composition. Consequently, the excess BMY 30047 is in suspension in the composition. If one only considers the solvent system of the oil phase and the active dissolved therein and excludes the active in suspension, the oil phase of the final composition is seen to be saturated with respect to the active. Thus such a suspension has a degree of unsaturation of 1. The present invention includes a composition which, though having less of the solvent system of the invention needed to dissolve all of the a primarily oil-soluble active in the oil phase of such composition, has an oil phase which is saturated with respect to the active actually solubilized. Excess active is suspended in such composition.

Formulations containing 1% BMY 30047 (11-cis, 13-cis-12-hydroxymethyl retinoic acid, delta lactone) developed in a vehicle (30047-C-03-A) similar to the marketed RETIN-A ® cream and in other experimental creams are shown in Table 4 and Table 5, respectively.

Figure 3:
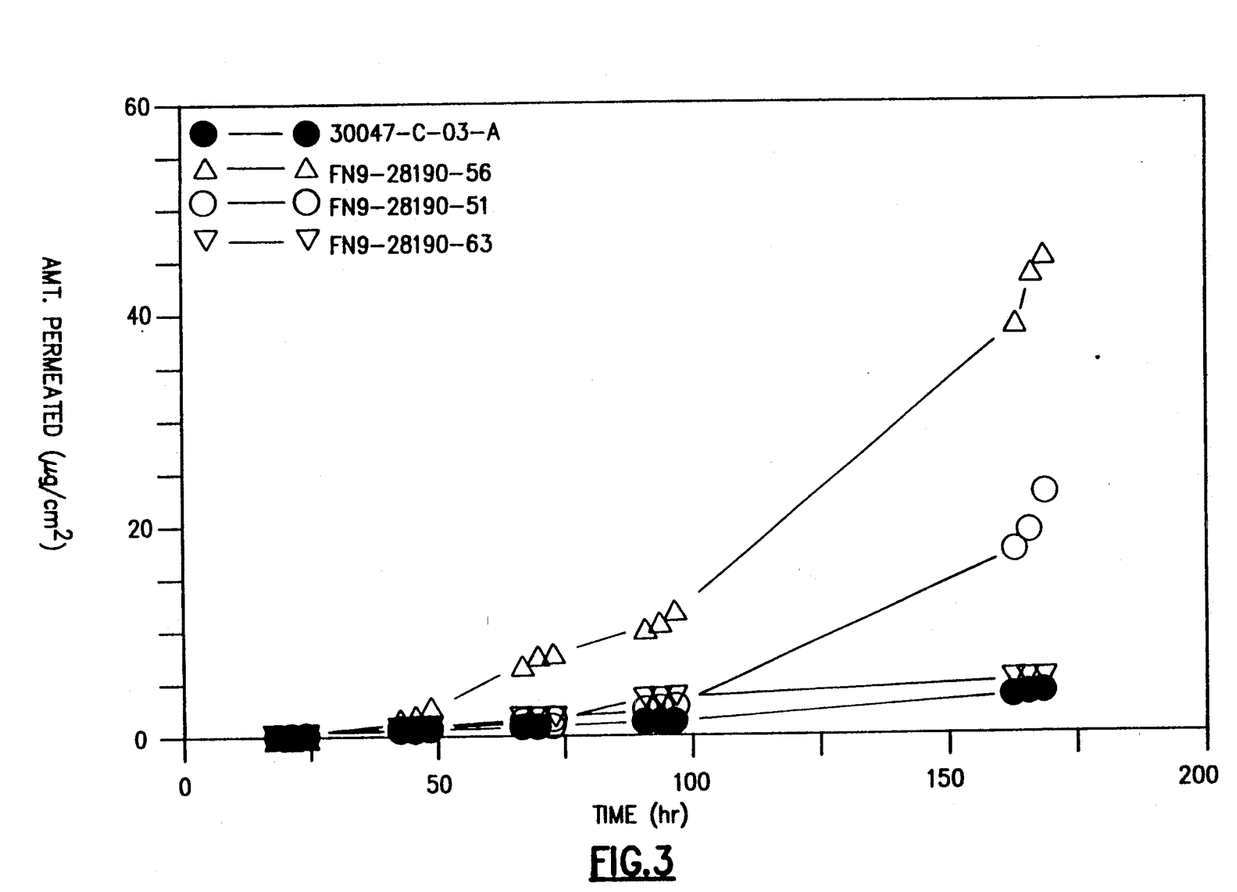
FIG. 3 shows the skin penetration of BMY 30047 from cream formulations FN9-28190-56, FN9-28190-51, FN9-28190-63 and 30047-C-03-A.

The in vitro human skin penetration of BMY 30047 from these formulations is shown in FIG. 3 and Table 6. The rank order of penetration is FN9-28140-56 cream>FN9-28150-51 cream>, FN9-28150-63 cream>, 30047-C-03-A cream.

FN9-28190-56 cream, containing 20 wt % DBA and 10 wt IPM, gave as much as nine times the skin penetration of BMY 30047 than that of the cream having 15 wt % IPM and 0.1 wt % sodium lauryl sulfate (30047-C-03-A) and the cream containing 10 wt % IPM, 20 wt % Capmul MCM and 0.1 wt % octoxynol-9 (FN9-28190-63).

The skin penetration of the cream containing 30 wt % DBA (FN9-28150-51) was about one-half the skin penetration of the cream containing 20 wt % DBA and 10 wt % IPM (FN9-28190-56) and about five times the penetration of the other two experimental creams.

It can be concluded from this study that dibutyl adipate enhances the skin penetration of BMY 30047 and that the skin penetration is further enhanced when isopropyl myristate is used in conjunction with dibutyl adipate. The data suggests that there is synergism in skin penetration enhancement when DBA and IPM are used together in accordance with the present invention.

TABLE 4

Composition of 1 wt % BMY 30047 Cream (30047-C-03-A)

| Ingredient | 30047-C-03-A % w/w | Rationale |
| --- | --- | --- |
| BMY 30047 | 1.00 | Active Ingredient |
| Stearic Acid | 18.00 | Thickening Agent |
| Isopropyl Myristate | 15.00 | Solvent/Emollient |
| PEG-40-Stearate | 5.00 | Emulsifying Agent |
| Stearyl Alcohol | 2.00 | Thickening Agent |
| Xanthan Gum | 0.60 | Thickening Agent |
| Sorbic Acid | 0.20 | Micropreservative |
| BHA | 0.10 | Antioxidant |
| BHT | 0.10 | Antioxidant |
| Sodium Lauryl Sulfate | 0.10 | Emulsifying Agent |
| Water for Production | 57.90 | Vehicle |

TABLE 5

Composition of 1 wt % BMY 30047 creams

| Ingredient | FN9-28190-56 | FN9-28190-51 | FN9-28190-63 | Rationale |
| --- | --- | --- | --- | --- |
| BMY 30047 | 1.00 | 1.00 | 1.00 | Active Ingredient |
| Dibutyl Adipate | 20.00 | 30.00 | — | Solvent/Emollient |
| Isopropyl Myristate | 10.00 | — | 10.00 | Solvent/Emollient |
| Capmul MCM* | — | — | 20.00 | Solvent/Emollient |
| Octoxynol-9 | — | — | 0.10 | Emulsifying Agent |
| Steareth-2 | 2.50 | 2.50 | 2.50 | Emulsifying Agent |
| Steareth-21 | 2.50 | 2.50 | 2.50 | Emulsifying Agent |
| Cetyl Alcohol | 2.00 | 2.00 | 2.00 | Thickening Agent |
| BHA | 0.075 | 0.075 | 0.075 | Antioxidant |
| BHT | 0.075 | 0.075 | 0.075 | Antioxidant |
| Stearyl Alcohol | 7.00 | 7.00 | 7.00 | Thickening Agent |
| Glyceryl Stearate | 1.00 | 1.00 | 1.00 | Emulsifying Agent |
| Laureth-4 | 1.00 | 1.00 | 1.00 | Emulsifying Agent |

TABLE 5-continued

| | Composition of 1 wt % BMY 30047 creams | | | |
|---|---|---|---|---|
| Ingredient | FN9-28190-56 | FN9-28190-51 | FN9-28190-63 | Rationale |
| Glycerin | 2.00 | 2.00 | 2.00 | Humectant |
| Na$_2$EDTA | 0.05 | 0.05 | 0.05 | Chelating Agent |
| Methyl Paraben | 0.20 | 0.20 | 0.20 | Micropreservative |
| Propyl Paraben | 0.20 | 0.20 | 0.20 | Micropreservative |
| Germall II* | 0.20 | 0.20 | 0.20 | Micropreservative |
| Water for Production | 50.20 | 50.20 | 50.20 | Vehicle |

TABLE 6

In-vitro skin penetration of 1.0 wt % BMY 30047 in different cream formulations.

| Formulation | Amount of BMY 30047 penetrated in 168 hours (micrograms/cm$^2$)** |
|---|---|
| FN9-28190-56 (20 wt % DBA + 10 wt % IPM) | 45.66 |
| FN9-28190-51 (30 wt % DBA) | 23.15 |
| FN9-28190-63 (CAPMUL MCM* 20 wt % + IPM 10 wt % + Octoxynol-9 0.1 wt %) | 5.33 |
| 30047-C-03-A (IPM 15 wt % + 0.1 wt % SLS)*** | 4.20 |

*Capmul MCM is glyceryl caprylate/caprate
**Average of 2 or 3 determinations
***SLS is sodium lauryl sulfate

EXAMPLE 5

Tretinoin is a primarily oil-soluble retinoid used topically for the treatment of acne. More recently, A. M. Kligman (U.S. Pat. No. 4,603,146), discloses the use of tretinoin in the treatment of photodamaged human facial skin. Tretinoin is marketed by Johnson & Johnson under the trade name RETIN-A ®.

Figure 4:
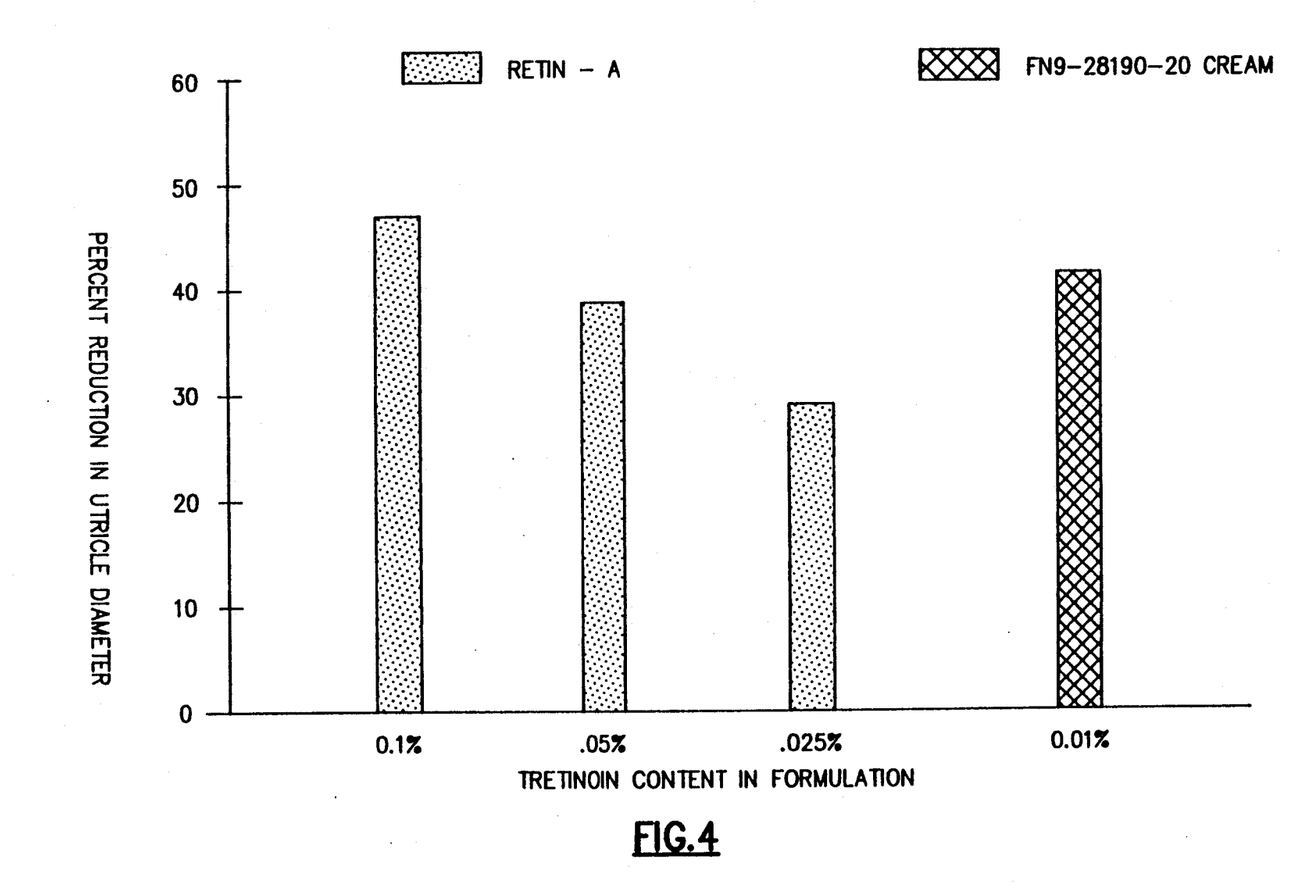
FIG. 4 shows the results of the rhino mouse assay of FN9-28190-20 in comparison to Retin A. ®

The composition of the experimental 0.01 wt % tretinoin cream formulation is given in Table 7. To evaluate the efficacy of tretinoin in the experimental formulations and compare same to that of the marketed RETIN-A ® cream, the formulations were evaluated in the rhino mouse uterine model. The test results are shown in FIG. 4. The rank order of efficacy is: RETIN-A ® cream (0.1 wt %) > FN9-28190-20 cream (0.01 wt %) = RETIN-A ® cream (0.05 wt %) > RETIN-A ® cream 0.025 wt %.

The FN9-28190-20 cream contains 3 wt % DBA, in an amount just sufficient to solubilize the tretinoin in the oil phase of the formulation. It is clear from this example that the formulation containing DBA increases the efficacy and hence the topical bioavailability of tretinoin. Although FN9-28190-20 cream contains a five-fold reduced amount of tretinoin, as compared to RETIN-A ® cream containing 0.05 wt % tretinoin, the FN9-28190-20 cream and the RETIN-A ® cream with 0.05% tretinoin have the same activity.

TABLE 7

The composition of 0.01 wt % tretinoin cream

| Ingredients | FN9-28190-20 % w/w | Rationale |
|---|---|---|
| Tretinoin | 0.01 | Active Ingredient |
| Dibutyl adipate | 3.00 | Solvent/Emollient |
| Mineral oil | 4.00 | Solvent/Emollient |
| Stearyl alcohol | 5.00 | Thickening Agent |
| Cetyl alcohol | 3.00 | Thickening Agent |
| Steareth-2 | 2.00 | Emulsifying Agent |
| Steareth 21 | 2.00 | Emulsifying Agent |
| Glyceryl Stearate | 1.00 | Emulsifying Agent |
| Laureth-4 | 1.00 | Emulsifying Agent |

TABLE 7-continued

The composition of 0.01 wt % tretinoin cream

| Ingredients | FN9-28190-20 % w/w | Rationale |
|---|---|---|
| BHA | 0.05 | Antioxidant |
| BHT | 0.05 | Antioxidant |
| Glycerin | 4.00 | Humectant |
| Citric acid | 0.004 | Chelating Agent |
| Kathon CG ® | 0.05 | Micropreservative |
| Germall II ® | 0.10 | Micropreservative |
| Water purified | 74.73 | Vehicle |

EXAMPLE 6

Ammonium lactate is the ammonium salt of lactic acid, an α-hydroxy acid. It is a primarily water-soluble active. It is marketed by Westwood-Squibb as Lac-Hydrin ® and is used for the topical treatment of xerosis and ichthyosis. R. J. Yu et al (U.S. Pat. No. 4,105,783) and E. J. Van Scott et al, (U.S. Pat. No. 4,234,599) disclose the use of α- or β-hydroxy acid or α-keto acids and esters thereof, their amides and ammonium salts, for therapeutic treatment of dry skin and skin keratoses.

The composition of experimental creams containing ammonium lactate equivalent to 30 wt % of lactic acid is given in Table 8. Three days prior to the in vitro skin penetration studies the experimental creams were homogeneously mixed with $^{14}$C-lactic acid (sodium salt) to produce an experimental cream having radioactivity of about 0.01 microCi per mg.

The in vitro human skin penetration data of lactic acid from these formulations is shown in Table 9. The rank order of penetrtation is: FN1-28393-46 > FN1-28393-45 > FN1-28393-47.

The FN1-28393-45 cream contains 5 wt % DBA. This cream showed about 1.4 times more skin penetration than FN1-28393-47 cream containing 5 wt % mineral oil.

The FN1-28393-46 cream contains 3 wt % DBA and 3 wt % IPM. This showed about 2.2 times more skin penetration than FN1-28393-47 cream containing 5% mineral oil.

It can be concluded from this study that dibutyl adipate enhances the skin penetration of primarily water-soluble actives such as lactic acid and that the skin penetration is further enhanced when isopropyl myristate is used in conjunction with dibutyl adipate.

As stated heretofore, the present inventor is unaware of any teaching or suggestion in the prior art that DBA, or a mixture of DBA and IPM, could be utilized to increase skin permeation of primarily water-soluble drugs. The fact that the solvent system of the present invention has such an effect is clearly demonstrated by this Example 6. Such effect holds true for primarily water-soluble topical drugs in general but is particularly noteworthy for alpha hydroxy acids, alpha keto acids and their respective esters and dermatologically acceptable salts (including inorganic alkali salts, organic base salts, ammonium salts, amino acid salts, pseudoamphoteric salts and amphoteric salts) and their corresponding enantiomers and racemates.

Although the present inventor does not wish to be limited to any one theory as to why the solvent system of the present invention surprisingly enhances skin permeation of both primarily oil-soluble drugs and primarily water-soluble drugs, one possible explanation may be that the solvent system disrupts or modifies the lipid and polar pathways of the skin in some manner thereby increasing the rate of permeation for both primarily water-soluble drugs and primarily oil-soluble drugs.

TABLE 8

Composition of experimental creams containing ammonium lactate equivalent to 30 wt % of lactic acid.

| Ingredients | FN1-28393-47 % w/w | FN1-28393-45 % w/w | FN1-28393-46 % w/w | Rationale |
| --- | --- | --- | --- | --- |
| Ammonium lactate | 53.00 | 53.00 | 53.00 | Active ingredient |
| Glyceryl stearate and PEG-100 stearate | 0.5 | 0.5 | 0.5 | Emulsifying agent |
| Mineral oil | 5.0 | — | — | Emollient |
| Dibutyl adipate | — | 5.0 | 3.0 | Emollient |
| Isopropyl myristate | — | — | 3.0 | Emollient |
| Dimethicone 200 | 1.0 | 1.0 | 1.0 | Emollient |
| Steareth-2 | 2.5 | 2.5 | 2.5 | Emulsifying agent |
| Steareth-21 | 2.5 | 2.5 | 2.5 | Emulsifying agent |
| Stearyl Alcohol | 3.5 | 3.5 | 3.5 | Thickening agent |
| Laureth-4 | 1.0 | 1.0 | 1.0 | Emulsifying agent |
| Cetyl alcohol | 0.5 | 0.5 | 0.5 | Thickening agent |
| Magnesium aluminum silicate | 2.0 | 2.0 | 2.0 | Thickening agent |
| Kathon CG ® | 0.05 | 0.05 | 0.05 | Micropreservative |
| Germall II ® | 0.2 | 0.2 | 0.2 | Micropreservative |
| Propylene glycol | 5.0 | 5.0 | 5.0 | Humectant |
| Water | 23.25 | 23.25 | 22.25 | Vehicle |

TABLE 9

In-vitro human skin penetration of different cream formulations containing ammonium lactate equivalent to 30 wt % of lactic acid.

| Formulation | Amount of $C^{14}$ lactic acid penetrated in 72 hours (DPM/$CM^2$)* | Amount penetrated in percentage relative to the formulation with mineral oil as a control |
| --- | --- | --- |
| FN1-28393-47 (Mineral oil 5 wt %) | 13004 | 100.00 |
| FN1-28393-45 (DBA 5 wt %) | 18115 | 139.30 |
| FN1-28393-46 DBA 3 wt % + IPM 3 wt %) | 28817 | 221.60 |

*The results are an average of multiple determination

EXAMPLE 7

Twenty - One Day Cumulative Irritation Tests In Humans

This test was conducted to evaluate the irritation and allergic potential of formulations containing DBA and IPM. This study method and modifications of same have been described in various publications. (A. M. Kligman and W. M. Wooding, A method for the measurement and evaluation of irritants on human skin, J. Invest. Dermatol., Vol. 49: pages 78-94, 1967; F. N. Marazulli and H. I. Maibach, in Dermatotoxicology, Ed. 2, Hemisphere Publishing Corporation, pages 167-296, 1983.) The composition of test formulations BMY 30047 1 wt % cream (30047-C-09-A) and its vehicle 30047-C-10-A cream are given in Table 10. Both test formulations contain 20 wt % DBA and 10 wt % IPM. These test formulations and two control formulations (0.5 wt % sodium lauryl sulfate and RETIN-A ® 0.1 wt % cream) were applied to 27 subjects, under an occlusive patch, for 21 consecutive days. Formulations were re-applied daily, except that patches applied on Saturday were left undisturbed until Monday. The Monday value was also recorded as the value for the immediately preceding Sunday. Skin reactions were scored on a 5-point grading scale as follows: 0=no sign of irritation; 1=slight erythema; 2=noticeable erythema with slight infiltration; 3=erythema with marked edema; 4=erythema with edema and blistering. Once a score of 4 was observed at any site, no further applications were made, and a score of 4 was assigned for the duration of the study. Results were reported by summing scores from all subjects and all visits. Relative irritation potential was estimated based on comparison with scores of the control compounds. The cumulative irritation potentials of the test formulations and the controls are given in Table 11. Both test formulations having DBA and IPM were classified as causing "no significant irritation" since they had very low cumulative irritation scores; whereas the control products RETIN-A ® 0.1 wt % cream and 0.5 wt % sodium lauryl sulfate had a cumulative score of 432.4 and 285.6, respectively, and were classified as "moderately irritating".

This study clearly demonstrates that the present invention provides skin penetration enhancement coupled with negligible side effects.

TABLE 10

Composition of BMY 30047 cream and its vehicle

| Ingredients | 30047-C-09-A % w/w | 30047-C-10-A % w/w |
|---|---|---|
| BMY 30047 | 1.0 | — |
| Dibutyl Adipate | 20.0 | 20.0 |
| Isopropyl Myristate | 10.0 | 10.0 |
| Steareth-2 | 2.5 | 2.5 |
| Steareth-21 | 2.5 | 2.5 |
| Stearyl Alcohol | 7.0 | 7.0 |
| Cetyl Alcohol | 2.0 | 2.0 |
| Glyceryl Stearate | 1.0 | 1.0 |
| Laureth-4 | 1.0 | 1.0 |
| BHA | 0.075 | 0.075 |
| BHT | 0.075 | 0.075 |
| Glycerin | 2.0 | 2.00 |
| Kathon CG ® | 0.05 | 0.05 |
| Germall II ® | 0.20 | 0.2 |
| Water for production | 50.60 | 51.60 |

TABLE 11

Results of 21-day cumulative irritation test in humans.

| Formulation | Cumulative Irritation Score |
|---|---|
| 30047-C-09-A cream (1 wt % BMY 30047 + 20 wt % DBA + 10 wt % IPM) | 30.9 |
| 30047-C-10-A cream vehicle (20 wt % DBA + 10 wt % IPM) | 24.8 |
| Retin A ® 0.1 wt % cream | 432.4 |
| 0.5 wt % sodium lauryl sulfate in petrolatum | 285.6 |

I claim:

1. A single or multiple phase topical composition for enhancing skin penetration of a pharmacologically active agent comprising:

a pharmacologically effective amount of a pharmacologically active agent, such agent being an oil-soluble steroid, retinoid or aretinoid or a water-soluble α- or β-hydroxycarboxylic acid, ketocarboxylic acid or ester, lactone or salt thereof; and (1) when the active agent is oil-soluble, an oil phase containing as a first solvent system, dibutyl adipate or a mixture of dibutyl adipate and isopropyl myristate, the oil-soluble active agent being solutiblized in the first solvent system, the first solvent system being present in an amount such that the oil-phase has a degree of unsaturation of 1 to 1.5 with respect to the oil-soluble active agent, any excess oil-soluble active agent not solubilized in the oil-phase being suspended in the composition; or (2) when the active agent is water-soluble,
 (i) a second oil phase containing as a second solvent system, dibutyl adipate or a mixture of dibutyl adipate and isopropyl myristate; and
 (ii) a water phase, the water-soluble active agent being solubilized in the water phase, any excess water-solublle active agent not solubilized in the water phase being solubilized in the second oil phase and/or suspended in the composition.

2. The composition as claimed in claim 1, wherein the active agent is oil-soluble and the first solvent system is present in an amount such that the oil phase has a degree of unsaturation of 1 with respect to the oil-soluble active agent.

3. The composition as claimed in claim 1, wherein the active agent is oil-soluble and the first solvent system is present in an amount such that the oil phase has a degree of unsaturation of 1.5 with respect to the oil-soluble active agent.

4. The composition as claimed in claim 1, wherein the active agent is oil-soluble and excess active agent not solubilized in the oil phase is present and is in suspension in the composition.

5. The composition as claimed in claim 1, wherein the first solvent system is dibutyl adipate and the second solvent system is dibutyl adipate.

6. The composition as claimed in claim 1, wherein the first solvent system is a mixture of dibutyl adipate and isopropyl myristate and the second solvent system is a mixture of dibutyl adipate and isopropyl myristate.

7. The composition as claimed in claim 1, wherein the dibutyl adipate is present in an amount of from about 0.1 wt % to about 99 wt %, based on the weight of the composition; and the isopropyl myristate is present in an amount 0 to about 99 wt %, based on the weight of the composition.

8. The composition as claimed in claim 7, wherein the dibutyl adipate is present in an amount of from about 0.1 wt % to about 50 wt %, based on the weight of the composition, and the isopropyl myristate is present in an amount of about 1 wt % to about 30 wt %, based on the weight of the composition.

9. The composition as claimed in claim 1, wherein the active agent is present in an amount from about 0.001 wt % to about 80 wt %, based on the weight of the composition.

10. The composition as claimed in claim 1, wherein the oil-soluble active agent is tretinoin, halobetasol propionate or 11-cis, 13-cis-12-hydroxymethyl retionic acid delta lactone and the water-soluble active agent is an α-hydroxycarboxylic acid or a dermatologically acceptable salt thereof.

11. The composition as claimed in claim 10, wherein the α-hydroxycarboxylic acid or dermatologically acceptable salt thereof is lactic acid, ammonium lactate or lysine lactate.

12. The composition as claimed in claim 1, wherein the active agent is water-soluble and excess active agent not solubilized in the water phase is present and is in suspension in the composition.

13. A method of obtaining in a warm blooded mammal an enhanced rate of skin penetration of a pharmacologically active agent selected from the group consisting of oil-soluble steroids, retinoids and aretinoids and water-soluble α- or β hydroxycarboxylic acid, ketocarboxylic acids, esters, lactones and salts thereof, comprising (a) contacting the sin of said mammal with a single or multiple phase topical composition comprising;
a pharmacologically effective amount of said active agent; and
when the active agent is oil-soluble, an oil phase containing as a solvent system, dibutyl adipate or a mixture of dibutyl adipate and isopropyl myristate, the oil-soluble active agent being solubilized in the oil phase, any excess oil-soluble active agent not solubilized in the oil phase being suspended in the composition; or
when the active agent is water-soluble,
 (i) a second oil phase containing as a second solvent system, dibutyl adipate or a mixture of dibutyl adipate and isopropyl myristate; and
 (ii) a water phase, the water-soluble active agent being solubilized in the water phase, any excess water-soluble active agent not solubilized in the water phase being solubilized in the second oil phase and/or suspended in the composition; and (b) when the active agent is oil-soluble, adjusting the amount of the solvent system and/or the relative amounts of dibutyl adipate and isopropyl myristate, when the solvent system is said mixture of dibutyl adipate and isopropyl myristate, so that the oil phase has a degree of unsaturation of 1 to 1.5 with respect to the oil-soluble active agent and the composition provides during said contacting an enhanced rate of skin penetration of the oil-soluble active agent; or when the active agent is water-soluble, adjusting the amount of the second solvent system and/or the relative amount of dibutyl adipate and isopropyl myristate, when the second solvent system is said mixture of dibutyl adipate and isopropyl myristate, so that the composition provides during said contacting an enhanced rate of skin penetration of the water-soluble active agent.

14. The method as claimed in claim 13, wherein the oil-soluble active agent is halobetasol propionate, tretinoin or 11-cis, 13-cis-12-hydroxymethyl retionic acid delta lactone.

15. The method as claimed in claim 13, wherein the water-soluble active agent is an α-hydroxycarboxylic acid or a salt thereof.

16. The method as claimed in claim 13, wherein the water-soluble active agent is lactic acid, ammonium lactate or lysine lactate.

17. A method for enhancing skin penetration of a pharmacologically active agent selected from the group consisting of water-soluble α-hydroxycarboxylic acids and dermatologically acceptable salts thereof and oil-soluble, halobetasol propionate, tretinoin, and 11-cis, 13-cis- 12-hydroxymethyl retionic acid delta lactone, the active agent being present in a dermatologically acceptable topical composition which, when the active agent is oil-soluble, has an oil phase or a water phase and an oil phase, or when the active agent is water-soluble, has an oil phase and a water phase, the active agent being solubilized in the oil phase when the active agent is halobetasol propionate, tretinoin, or 11-cis, 13-cis-12-hydroxymethyl retionoic acid delta lactone or solubilized in the water phase when the active agent is an α-hydroxycarboxylic acid or a dermatologically acceptable salt thereof; which method comprises:

incorporating in said composition a skin penetration enhancing amount of dibutyl adipate or a mixture of isopropyl myristate and dibutyl adipate, provided that, when the active agent is halobetasol propionate, tretinoin, or 11-cis, 13-cis-12-hydroxymethyl retionic acid delta lactone, the amount of the dibutyl adiptate, or the mixture of isopropyl myristate and dibutyl adipate, employed results in the oil phase of the composition having an unsaturation of 1 to 1.5 with respect to the oil-soluble active agent and the composition having an enhanced rate of skin penetration of the oil-soluble active; and when the active agent is an α-hydroxycarboxylic acid or a dermatologically acceptable salt thereof, the amount of the dibutyl adipate, or the mixture of isopropyl myristate and dibutyl adipate, results in the composition having an enhanced rate of skin penetration of the water-soluble active agent.

* * * * *